(12) United States Patent
Demais et al.

(10) Patent No.: US 7,758,691 B2
(45) Date of Patent: Jul. 20, 2010

(54) INTERCALATED CLAYS

(76) Inventors: Herve Demais, Lann Kerdrean, Brandivy (FR) 56390; Jocelyne Brendle, 8 rue des Merles, Wittenheim (FR) 68270; Herve Le Deit, 10 Chemin de la Fontaine, Saint Pierre - Servel, Lannion (FR) 22300; Anca Laza, 7 rue de France, Brunstatt (FR) 68530; Luc Lurton, 79 rue de Pen-lan, Pleubian (FR) 22610; Dominique Brault, 7 rue du Trieux, Lezardrieux (FR) 22740

( * ) Notice: Subject to any disclaimer, the term of this patent is extended or adjusted under 35 U.S.C. 154(b) by 84 days.

(21) Appl. No.: 11/574,871

(22) PCT Filed: Jan. 21, 2005
(Under 37 CFR 1.47)

(86) PCT No.: PCT/FR2005/000145
§ 371 (c)(1),
(2), (4) Date: Feb. 11, 2008

(87) PCT Pub. No.: WO2006/030075
PCT Pub. Date: Mar. 23, 2006

(65) Prior Publication Data
US 2008/0213455 A1     Sep. 4, 2008

(30) Foreign Application Priority Data
Sep. 9, 2004   (FR) .................... 04 09583

(51) Int. Cl.
C08K 9/06    (2006.01)
C08K 5/00    (2006.01)
A23K 1/00    (2006.01)
B32B 1/00    (2006.01)

(52) U.S. Cl. .............. 106/487; 106/486; 424/63; 424/69; 424/195.17; 426/615; 426/655; 501/141; 524/9

(58) Field of Classification Search ............. 106/486, 106/487; 424/63, 69, 195.17; 426/615, 655; 501/141; 524/9
See application file for complete search history.

(56) References Cited

U.S. PATENT DOCUMENTS

| 3,901,976 A |   | 8/1975  | Roth et al. |
| 4,888,185 A |   | 12/1989 | Miller et al. |
| 5,578,672 A | * | 11/1996 | Beall et al. ............... 524/446 |
| 6,287,575 B1 | * | 9/2001 | Walker et al. ............ 424/262.1 |
| 6,287,576 B1 | * | 9/2001 | Bgatov et al. ............ 424/400 |

FOREIGN PATENT DOCUMENTS

| FR | 2406395 A1 | 5/1979 |
| JP | 6-256761 A * | 9/1994 |
| WO | 96/25055 A1 | 8/1996 |
| WO | WO2005/068364 A1 * | 7/2005 |

OTHER PUBLICATIONS

"La Soupe en engraissement: des auges propres et des porcs qui poussent", PORC Magazine, Feb. 2003, pp. 134-137, vol. 363, PORC Magazine, Rennes, FR, XP00118033.

* cited by examiner

Primary Examiner—Anthony J Green
(74) Attorney, Agent, or Firm—McLeland Patent Law Office, PLLC

(57) ABSTRACT

The invention relates to interspersed clay, comprising clay and a seaweed extract used as an interspacing component, particularly an ulva extract. The invention also relates to a method for the preparation thereof and to foodstuffs and nanocomposites comprising said interspersed clay.

17 Claims, No Drawings

INTERCALATED CLAYS

The present invention relates to compositions which are based on clay and algae extracts.

Clays are rocks which are composed principally of sheet silicates (phyllosilicates) which are hydrated to a greater or lesser extent. Phyllosilicates are compounds of the orthosilicate anion in which the tetrahedrons share three of their oxygens between them, the fourth always being directed at the same side of the sheet which is formed in this manner. The structure may be illustrated as a two-dimensional assembly having two types of geometric shape: octahedron and tetrahedron. Three types of phyllosilicates are defined in this manner:

the so-called 1:1 phyllosilicates whose sheet is constituted by the juxtaposition of a tetrahedric layer with an octahedric layer. The thickness of this type of sheet is 0.70 nm. Kaolinite is the most representative compound of this group, the so-called 2:1 phyllosilicates whose sheet is constituted by an octahedric layer between two tetrahedric layers. The thickness of this type of sheet is 0.96 nm, the so-called 2:1:1 phyllosilicates whose sheet is constituted by a layer of brucite $Mg(OH)_2$ or gibbsite $Al(OH)_3$ in the interlamellar space. The thickness of this type of sheet is 1.4 nm.

2:1 phyllosilicates have the most advantageous properties, due to their structure. The cavities of the tetrahedric layer of a sheet substantially contain silicon ions and the cavities of the octahedric layer contain aluminum or magnesium ions. However, a number of substitutions may take place in the different layers. The silicon ions are substituted by trivalent cations. The aluminum or magnesium ions are substituted by tri- or divalent ions. These substitutions introduce an excess of negative charge into the sheet. It is compensated for by the presence of cations in the interfoliar space. These cations may be exchanged for other cations of mineral or organic origin. The thickness of the interfoliar space can thus be adjusted in accordance with the intended application. Thus, various methods for modifying the structure of phyllosilicates have been used:

the bridging method: processing in two steps which is intended to first replace the interfoliar cations with polycations (based on aluminum $[Al_{13}O_4(OH)_{24}(H_2O)_{12}]^{7+}$ (Diddams P. A., Thomas, J. M., Jones, W., Ballantine, J. A. and Purnell, J. (1984), Chem. Soc. Chem. Commun, 106, 1340), zirconium $[Zr_4(OH)_{12}(H_2O)_{12}]^{4+}$, (Yamanaka S. and Brindley, G. W. (1979) Clays and Clay Minerals, 27, 119), then calcinating the compound obtained at a temperature which is sufficient to transform the polycations into pseudo oxide particles. The bridged phyllosilicates (also referred to as pillared phyllosilicates) obtained using this method are two-dimensional porous solids which have a pore radius which covers a wide range (1.5 to 10.0 nm) and a significant catalytic activity which is linked to the acid sites of both the sheets and the pillars.

The transformation of hydrophilic phyllosilicates into organophilic phyllosilicates (A. Weiss (1963) Angew. Chem. Internat. Edit., 2, 134). The processing involves introducing organic cations (such as, for example, alkylammonium ions having the formula $CH_3-(CH_2)_n-NH_3^+$, where n is between 1 and 20) into the interfoliar space by means of ion exchange. In this case, the thickness of the interfoliar space depends both on the nature of the phyllosilicate, the location of the charge and the number of carbon atoms present in the carbon chain.

These organophilic phyllosilicates become compatible with polymer matrices and are used as charges in the polymers. There are currently three categories of compositions of the type phyllosilicate/polymer (Alexandre, M. and Dubois, P. (2000), Mater. Sci. En., 28, 1).

Composites which are referred to as microcomposites, in which the polymer does not penetrate into the interfoliar space of the phyllosilicate. This acts as a reinforcement.

Intercalated (interspersed) nanocomposites in which the polymer is inserted between the sheets.

Exfoliated nanocomposites in which the sheets of a nanometric size are completely dispersed in the polymer matrix, thus forming a monolithic structure on a microscopic scale.

Exfoliated nanocomposites are especially advantageous insofar as the phyllosilicate/polymer interactions are at a maximum, the entire surface-area of the sheets being available in this instance. The properties in terms of mechanics, fire-resistance, thermal stability and the barrier properties (permeability with respect to gas and hydrocarbons) can thus be improved.

The main methods for obtaining nanocomposites are as follows:

by means of polymerisation in situ (Okada, A., Kawasumi, M., Usuki, A., Kojima, Y., Kurauchi, T. and Kamigaito (1990) Mater. Res. Soc. Pro., 171, 45.): a method in two steps which involves first swelling an organophilic phyllosilicate in a monomer solution, and then adding thereto a treatment agent in order to initiate the polymerisation. During the swelling, the molecules of polar monomers will diffuse between the sheets. The alkylammonium ions present in the interfoliar space will be directed perpendicularly relative to the sheets in order to optimise the interactions with the monomer. The addition of the processing agent brings about the polymerisation which causes the exfoliation of the phyllosilicate.

By means of forming sheet silicates in situ (Carrado, K. and Xu, L. Q; (1998) *Chem. Mater.*, 10, 1440-1445): this recent method involves carrying out a hydrothermal crystallisation in situ of sheet silicates, such as hectorite, in an aqueous polymer gel.

In solution: in this case, the organophilic lamellar compound is exfoliated using an adequate organic solvent in which the polymer is soluble. The entropy gain obtained by means of the desorption of solvent molecules will allow the polymer chains to diffuse between the clay sheets. The solvent is then evaporated.

By means of fusion (Vaia, R. A. Ishii, H. and Giannelis, E. P. (1993) Chem. Mater, 5, 1694): the organophilic phyllosilicate is in this case mixed with the polymer. The whole is melted then annealed at a temperature greater than the vitreous transition temperature, a process which leads to the formation of the nanocomposite.

In parallel with these methods, a method using photochemical means has also been used (Koch, T., Menning, M. and Schmidt, H. (1999) *Adv. Sci. Technol.*, 17, 681, Zahouily, K., Benfahri, S., Bendaikha, T., Baron, J. and Decker, C. (2001) Proc. RadTech Europe, 583). It involves irradiating, under UV, a formulation comprising a monomer (for example an acrylic monomer), a polymerisation photoinitiator, a reactive diluent and an organophilic phyllosilicate. It was thus possible to prepare a transparent and non-coloured nanocomposite which further has physio-chemical properties which are stronger than that of the resin alone by using a polyurethane-acrylate resin. This method, which is carried out at ambient temperature and in the absence of solvents has the advantage of being both simple to implement and environmentally friendly.

The formation of porous heterostructures: a new method for obtaining compounds comprising siliceous entities in the interfoliar space of smectites (Galarneau, A., Barodawalla, A. and Pinnavaia, T. J. (1995) *Nature*, 174, 529.) is based on the assembly of silica around micelles of a surfactant within the actual interfoliar space. The formation mechanism proposed by the authors is similar to that which leads to mesoporous solids of the MCM-41 type. The advantage of the compounds formed in this manner is that they have a pore size and a specific surface-area greater than those required for pillar compounds. The operating method requires three steps:

the first involves introducing an alkylammonium ion (for example, the hexadecyltrimethylammonium ion, designated $C_{16}TMA$) in the interfoliar space by means of ion exchange;

the second is intended to incorporate a primary amine (such as dodecylamine) and a silica precursor (tetraethylorthosilicate, TEOS);

the last step involves releasing the porosity by means of calcination or by means of extraction of the surfactant in an acidified solvent.

In the first case, the oxidation of the organic material brings about the formation of the protons required for the electric neutrality of the framework. These materials thus have an intrinsic acidity, a property which allows a number of catalytic applications to be envisaged (EP 1044721), J. A. Martens, E. Benazzi, J. Brendlé, S. Lacombe and R. Le Dred, *Stud. Surf. Sci. Catal.*, 2000, 130, 293).

In the second case, the Si—OH groups are retained. It is consequently possible to functionalise these compounds by means of grafting (Mercier, L. and Pinnavaia, T. J. (1998) *Microporous and Mesoporous Materials* 20, 101).

Their cationic exchange properties aside, phyllosilicates are also known for their properties of adsorption. They readily form lamellar complexes by means of insertion of organic or water molecules in the interfoliar space. This phenomenon, which is referred to as swelling, depends on the charge of the sheet, the location thereof (tetrahedric or octahedric layer), and the nature of the compensation cations. Divalent cations, such as $Mg^{2+}$ and $Ca^{2+}$ facilitate the adsorption of water in the interfoliar space by forming macro cations.

The adsorption of organic molecules may confer a hydrophobic character to the phyllosilicate.

Finally, some phyllosilicates have acid properties, the acidity being connected, for example, to the substitution of silicon ions of the tetrahedric layer by aluminum ions. The first acidity, which is referred to as Bröonsted acidity, originates either from the presence of protons in the interfoliar space, or the dissociation of molecules of hydration water surrounding the compensation cations. The second acidity, referred to as Lewis acidity, is less common: it results from the existence of faults or fracture lines in the structure of the sheet.

The acidity of phyllosilicates is the reason for their catalytic properties. They may undergo a prior treatment in order to improve their catalytic activity: either by means of acid treatment, as in the case of the commercial montmorillonite K10, or by means of cation exchange.

Montmorillonite is currently the most studied and most used 2:1 phyllosilicate. It substantially contains the elements silicon, aluminum and magnesium. It is part of the smectite group and dioctahedric sub-group.

The theoretical structural formula thereof is:

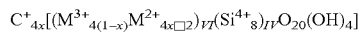

($C^+$: compensation cations of the interfoliar space, $M^{3+}$: trivalent cation, such as $Al^{+3}$, $Fe^{+3}$, $M^{2+}$: divalent cation, such as $Mg^{+2}$, $Cu^{+2}$, $Co^{+2}$, $Zn^{+2}$, $Fe^{+2}$, $Ni^{+2}$, x: level of octahedric substitution, $\square$: lacuna in octahedric layer.

In reality, a natural montmorillonite often contains tetrahedric substitutions in addition to octahedric substitutions.

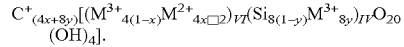

(y: level of tetrahedric substitution).

The synthesis thereof in pure phase has recently been described (M. Reinholdt, J. Miehé-Brendlé, L. Delmotte, A. -M. Flank, R. Cortès, M. -H. Tuilier. and R. Le Dred, *Eur. J. Inorg. Chem.*, 2001, 11, 2831.)

An object of the present invention is to provide an intercalated (interspersed) clay which comprises an algae extract as an intercalation compound (interspersing compound) An object of the invention is also to provide a method for preparing intercalated clays which are intended in particular for the preparation of clay/polymer nanocomposites and foodstuffs for animals.

In the context of the invention, the term "algae" is intended to refer to all marine plant types which comprise polysaccharides which are soluble in water and especially algae of the ulva type (ulvas algae). These algae are known to proliferate on coasts, in particular Atlantic and Mediterranean coasts, causing them to be referred to as the "green tide". They constitute a raw material which is available and readily accessible and whose value is being researched.

Furthermore, some constituents, especially polysaccharides which are soluble in water, extracted from these algae are advantageous as a nutriment and as a polymer material in cosmetics and pharmaceutics.

In the context of the invention, the algae extracts used are preferably extracts of ulva algae. The algae extracts preferably comprise ulvanes, in particular more than 80% by weight. The chemical structure of these ulvane polysaccharides is still not completely clear. However, it is known that they are compounds of units of rhamnose, xylose, glucose, glucoronic acid and sulphate.

The term "clay" is intended to refer to a phyllosilicate of natural or synthetic origin having an appropriate structure for the intercalation (interspersing) of compounds. These clays are preferably clays which have a sheet structure, such as montmorillonites, beidellite, saponite, illites, glauconite, chlorites, vermiculite, fibrous clays. A clay is preferably used which has swelling properties (smectite) and in particular montmorillonite. Of course, it may be envisaged to make use of a mixture of a plurality of clays.

The interspersion between clay and algae extracts is preferably carried out by mixing in an aqueous phase a clay and the algae extract in a weight ratio (dry extract) clay/algae extract of from 0.1 to 80, preferably from 1 to 30, more preferably from 2 to 15.

According to another aspect, the invention relates to a method for preparing an intercalated clay using an algae extract comprising the steps consisting in:
i) preparing an aqueous algae extract;
ii) contacting the extract with a clay in an appropriate solvent for a sufficient length of time; and
iii) isolating the intercalated clay obtained.

The agitation time of the clay/algae extract admixture is between 30 seconds and 72 hours, preferably between 1 minute and 36 hours and even more preferably between 2 minutes and 24 hours. Following the mixing, the solid phase of the suspension is separated, for example, centrifuged. The solid collected is washed and then dried.

Clays which are intercalated in this manner with algae extracts have a spacing between sheets which may be up to 30 Å. This large spacing makes them very advantageous for a large number of applications.

Especially, they may act in the unmodified state as an absorber of voluminous compounds which are difficult for other materials to take up. This type of compound includes in particular some toxins, such as mycotoxins. In this manner, the intercalated clays described may be used by way of a supplement in animal or human foodstuffs.

Thus, according to another aspect, the invention relates to the use of the intercalated clay, in particular in animal and human foodstuffs, cosmetics, pharmaceutics, plastics technology, in road surfacings and packagings which may or may not be for foodstuffs.

These properties may especially be used in animal foodstuffs in order to improve the foodstuff yield with an incorporation of intercalated clay in the order of from 0.01 to 1% by weight in the foodstuff.

According to another aspect, the invention therefore relates to animal foodstuffs which preferably comprise from 0.01 to 2% by weight, and especially between 0.05 and 1% by weight, of intercalated clay as described above.

The spacing of the sheets also allows the interfoliar space to be made accessible for other functionalities, such as grafting of radicals for activating chemical or biochemical reactions.

The products originating from the present invention have an interfoliar space which is accessible, in contrast to what can be observed in the case of intercalation with other polymers (Intercalation de chitosan, extrait de carapaces de crustacés, dans une argile)(Intercalation of chitosan or extract of crustacean shells in a clay), M. Darder et al., Chem. Mater. 2003, 15, 3774-3780). It can therefore very readily be contemplated to bring other compounds into the structure, which affords the possibility in particular for the synthesis of environmentally friendly nanocomposites which can be used in a large number of fields, such as animal and human foodstuffs, cosmetics, pharmaceutics, plastics technology, packagings which may or may not be for foodstuffs, road surfacings, etc . . . .

According to another aspect, the invention therefore relates to nanocomposites which comprise the intercalated clay described and a natural or synthetic polymer.

The invention will be described in greater detail by the way of the following examples.

EXAMPLES

Example 1

Preparation of an Na montmorillonite having a tetrahedric substitution level equal to 0.4 (M. Reinholdt, J. Miehé-Brendlé, L. Delmotte, A. -M. Flank, R. Cortès, M. -H. Tuilier and R. Le Dred, *Eur. J. Inorg. Chem.,* 2001, 11, 2831).

A montmorillonite having the chemical formula:

$Na_{0.4}[Al_{1.6}Mg_{0.4}]Si_4O_{10}(OH_{1.8}F_{0.2})$ is prepared in the following manner:

8.1 g of a solution of 5% hydrofluoric acid (HF, Fluka) in water are added with magnetic agitation to 685.86 g of distilled water placed in a beaker of PTFE. 8.64 g of magnesium acetate (Mg(CH$_3$COO)$_2$, Aldrich), 1.74 g of sodium acetate (Na(CH$_3$COO, Fluka), 10.53 g of pseudobohmite (Al$_2$O$_3$, Condéa) and 24.3 g of silica (SiO$_2$ Aerosil 130, Degussa) are successively added to the reaction medium with agitation. The whole is matured with agitation at ambient temperature for two hours before being poured into a pressure vessel coated with PTFE and placed in an oven at 220° C. for 72 hours. The pressure vessel is then cooled to ambient temperature and the product of the reaction is filtered over a Büchner. After three successive washes in distilled water, the product is dried for 24 hours at 60° C.

Example 2

Preparation of Ulvane

Method for extracting ulvanes (Lahaye, M., Birnalendu R., Baumberger, S., Quernener, B. and Axelos, M. (1996) Hydrobiologia, 326/327, 473).

The ulva which has been dried and ground (34.4 g) in suspension in water (500 mL) is brought to reflux for 1 hour. The suspension is centrifuged (10.24×g, 20 min) and the insoluble is recovered and then extracted again under the same conditions as before. The suspension is centrifuged. The two supernatants of these two extractions are recombined, filtered, then the ulvane in solution is precipitated in alcohol at 95° C. The product is then dried.

Example 3

Incorporation of Ulvanes in the Interfoliar Space of Synthesised Na-Montmorillonite.

1 g of Na-montmorillonite prepared according to example 1 is placed in suspension in 100 mL of distilled water (solution A). The whole is placed under magnetic agitation at ambient temperature for 24 hours. In parallel, 5 g of ulvanes prepared according to example 2 are dispersed in 50 ml of distilled water with magnetic agitation at ambient temperature for 24 hours (solution B). Solution A is then mixed with solution B and the whole is left under magnetic agitation for 24 hours at ambient temperature. The suspension is then centrifuged for 10 minutes (at a speed of 20000 rpm). The solid collected is then placed in suspension in 20 mL of distilled water, then separated by means of centrifuging. This washing is repeated twice. The solid is then dried in air for 24 hours. The product formed in this manner contains 29% of organic material. The interfoliar spacing is 3.8 nm.

The invention claimed is:

1. An intercalated clay, comprising a clay and an algae extract as an intercalation compound, and having an interfoliar spacing of up to 30 Å.

2. The clay of claim 1, wherein the algae extract is an ulva algae extract.

3. The clay of claim 1, wherein the algae extract comprises ulvanes.

4. The clay of claim 1, wherein the algae extract comprises more than 80% by weight of ulvanes.

5. The clay of claim 1, wherein the clay is a sheet clay.

6. The clay of claim 1, wherein the clay has swelling properties.

7. The clay of claim 1, wherein the clay is a montmorillonite.

8. The clay of claim 1, wherein the weight ratio clay/algae extract is from 0.1 to 80.

9. Animal foodstuffs comprising from 0.01 to 2% by weight of the intercalated clay of claim 1.

10. A nanocomposite comprising the intercalated clay of claim 1 and a natural or synthetic polymer.

11. A foodstuff for animals or humans, comprising the intercalated clay of claim 1.

12. A cosmetic comprising the intercalated clay of claim 1.

13. A pharmaceutical composition comprising the intercalated clay of claim 1.

14. A plastics technology component comprising the intercalated clay of claim 1.

15. A road surfacing component comprising the intercalated clay of claim 1.

16. A packaging component comprising the intercalated clay of claim 1.

17. A method for preparing an intercalated clay using an algae extract, comprising the steps of:
 i) preparing an aqueous algae extract;
 ii) contacting the extract with a clay in a solvent for 30 seconds to 72 hours ; and
 iii) isolating the intercalated clay obtained.

* * * * *